(12) United States Patent
Richard

(10) Patent No.: US 10,307,349 B2
(45) Date of Patent: *Jun. 4, 2019

(54) APPARATUS AND METHOD FOR PREPARING COSMECEUTICAL INGREDIENTS CONTAINING EPI-DERMAL DELIVERY MECHANISMS

(71) Applicant: PPP&C INC., West Hollywood, CA (US)

(72) Inventor: David A. Richard, Shingle Springs, CA (US)

(73) Assignee: PPP&C INC., West Hollywood, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/460,088

(22) Filed: Mar. 15, 2017

(65) Prior Publication Data

US 2017/0181936 A1    Jun. 29, 2017

Related U.S. Application Data

(63) Continuation of application No. 14/971,320, filed on Dec. 16, 2015.

(51) Int. Cl.

| | |
|---|---|
| *A61K 8/06* | (2006.01) |
| *A61K 8/14* | (2006.01) |
| *A61K 8/41* | (2006.01) |
| *A61K 8/55* | (2006.01) |
| *A61K 8/63* | (2006.01) |
| *A61K 8/73* | (2006.01) |
| *A61Q 19/00* | (2006.01) |
| *A61Q 19/08* | (2006.01) |

(52) U.S. Cl.
CPC .................. *A61K 8/06* (2013.01); *A61K 8/14* (2013.01); *A61K 8/416* (2013.01); *A61K 8/553* (2013.01); *A61K 8/63* (2013.01); *A61K 8/735* (2013.01); *A61Q 19/00* (2013.01); *A61Q 19/08* (2013.01); *A61K 2800/70* (2013.01); *A61K 2800/805* (2013.01)

(58) Field of Classification Search
CPC .... A61K 8/06; A61K 2800/805; A61K 31/66; A61K 8/735; A61K 8/63; A61K 8/553; A61K 8/416; A61K 8/14; A61K 2800/70; A61Q 19/00; A61Q 19/08
See application file for complete search history.

(56) References Cited

U.S. PATENT DOCUMENTS

| | | | | |
|---|---|---|---|---|
| 5,733,572 | A | * | 3/1998 | Unger ...................... A61K 8/14 424/1.21 |
| 5,882,675 | A | | 3/1999 | Ninomiya |
| 2013/0069261 | A1 | * | 3/2013 | Hwang .................. A61K 9/127 264/4.1 |

FOREIGN PATENT DOCUMENTS

CN         103989635        *   8/2014

OTHER PUBLICATIONS

Prausnitz MR, Langer R. Transdermal drug delivery. Nat Biotech. 2008; 26 (11):1261-1268.
Thong HY, Zhai H, Maibach HI. Percutaneous penetration enhancers: an overview. Skin Pharmacol Physiol 2007; 20 (6):272-282.
Michaels AS, Chandrasekaran SK, Shaw JE. Drug permeation through human skin. Theory and in vitro experimental measurement. AIChE J. 1975; 21(5):985-996.
Albery WJ, Hadgraft J. Percutaneous absorption: in vivo experiments. J Pharm Pharmacol.1979; 31(3):140-147.
Tojo K. Random brick model for drug transport across stratum corneum. J Pharm Sci. 1987; 76 (12):889-891.

* cited by examiner

*Primary Examiner* — Snigdha Maewall
(74) *Attorney, Agent, or Firm* — Inventive Law Inc.; Jim H. Salter

(57) ABSTRACT

The skin serves as a barrier that protects the body from the external environment and prevents water loss. This barrier function also prevents most hydrophilic or hydrophobic and large molecular weight ingredients (>500 kDa) from penetrating intact skin. Until recently, methods to increase stratum corneum permeability were generally not effective enough to make the stratum corneum so permeable that the barrier posed by the viable epidermis mattered. However, that has now changed with the development of the present embodiment's physical methods and highly optimized chemical formulations, such that we revisited the permeability of the full epidermis with the example embodiment's constructs and not focus only on the stratum corneum. This example embodiment therefore tests the hypothesis that the viable epidermis offers a significant permeability barrier to both small molecules and macromolecules that becomes the rate limiting step.

21 Claims, 7 Drawing Sheets

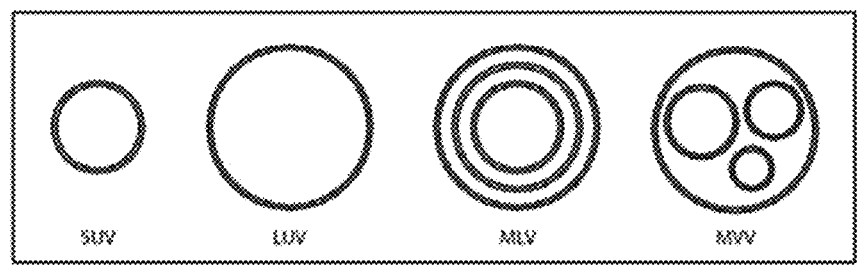
Figure 1.0
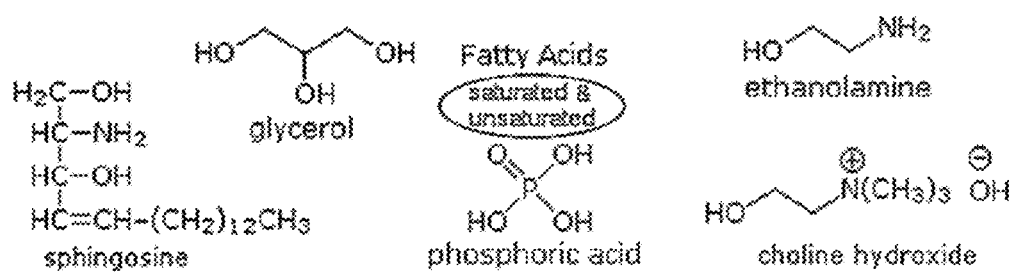
Figure 2.0

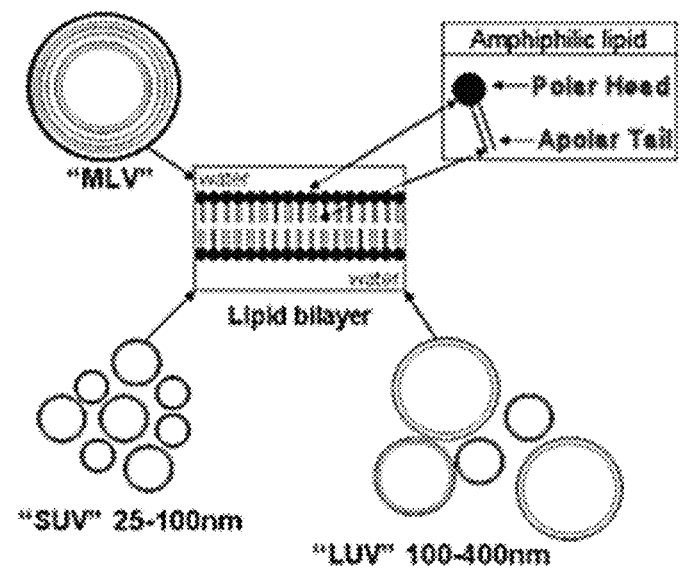
Figure 3.0
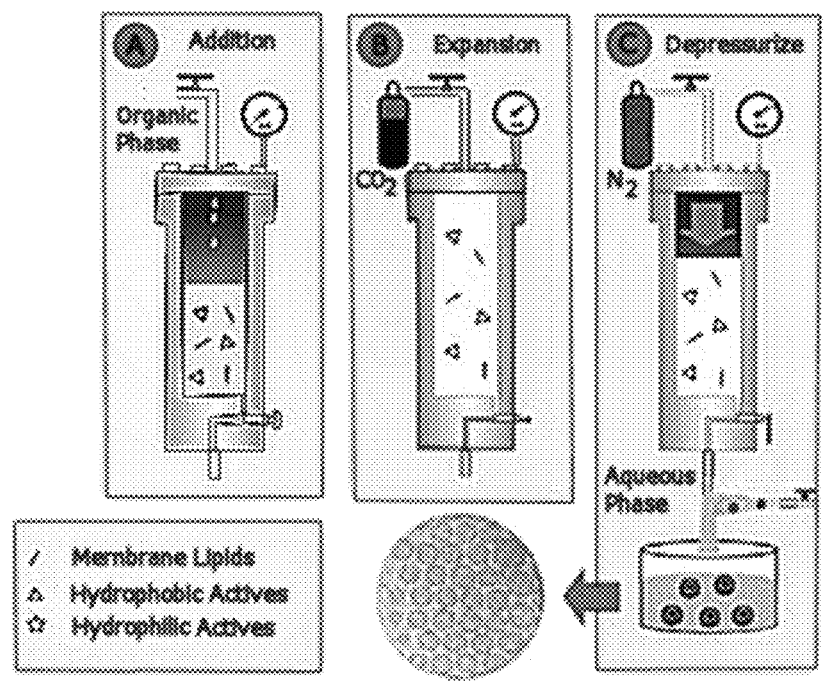
Figure 4.0 A, B, C

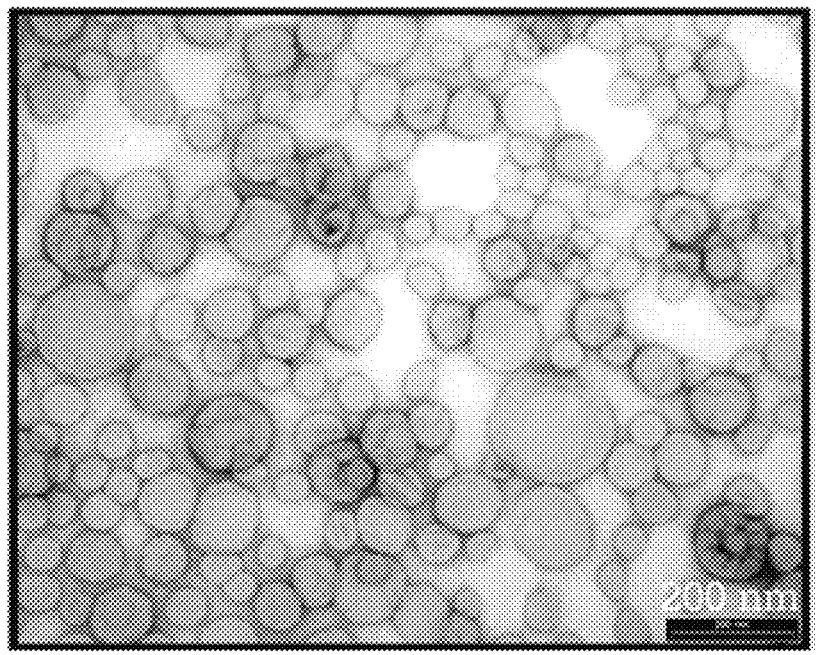
Figure 5.0
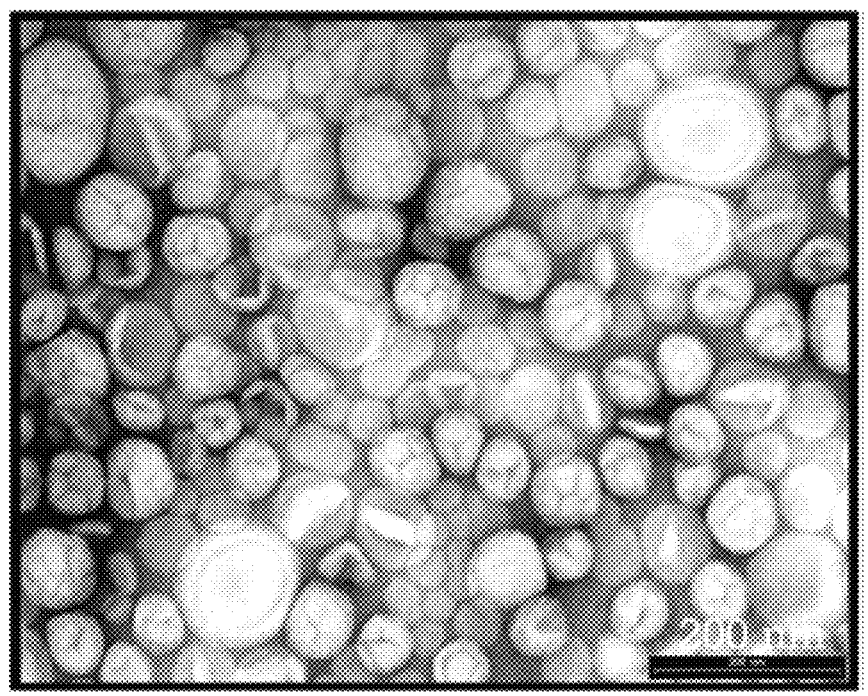
Figure 6.0

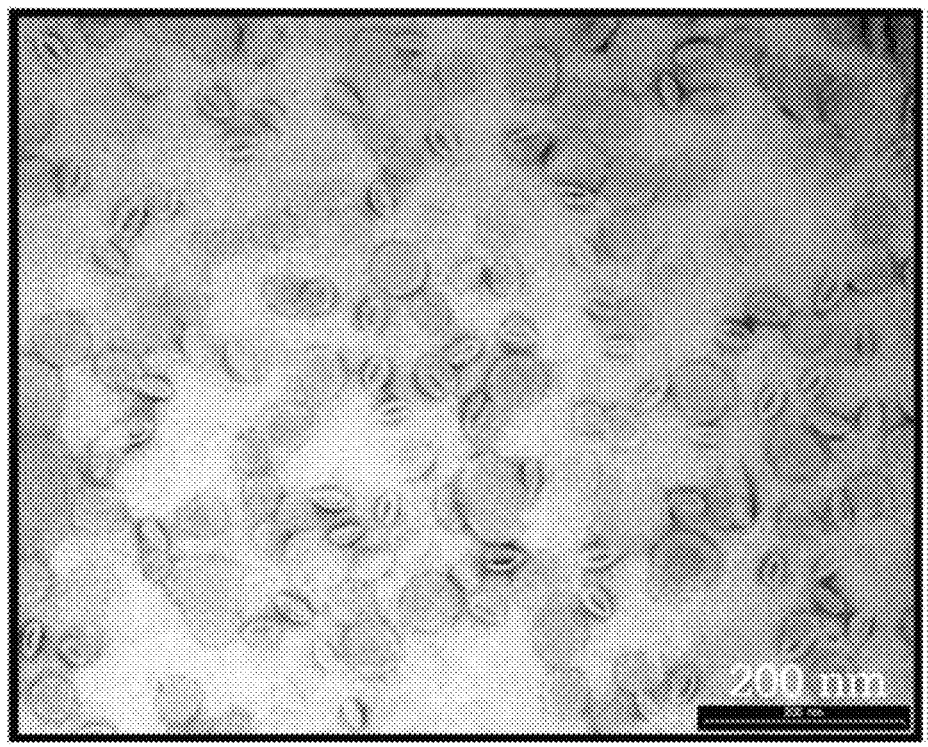
Figure 7.0

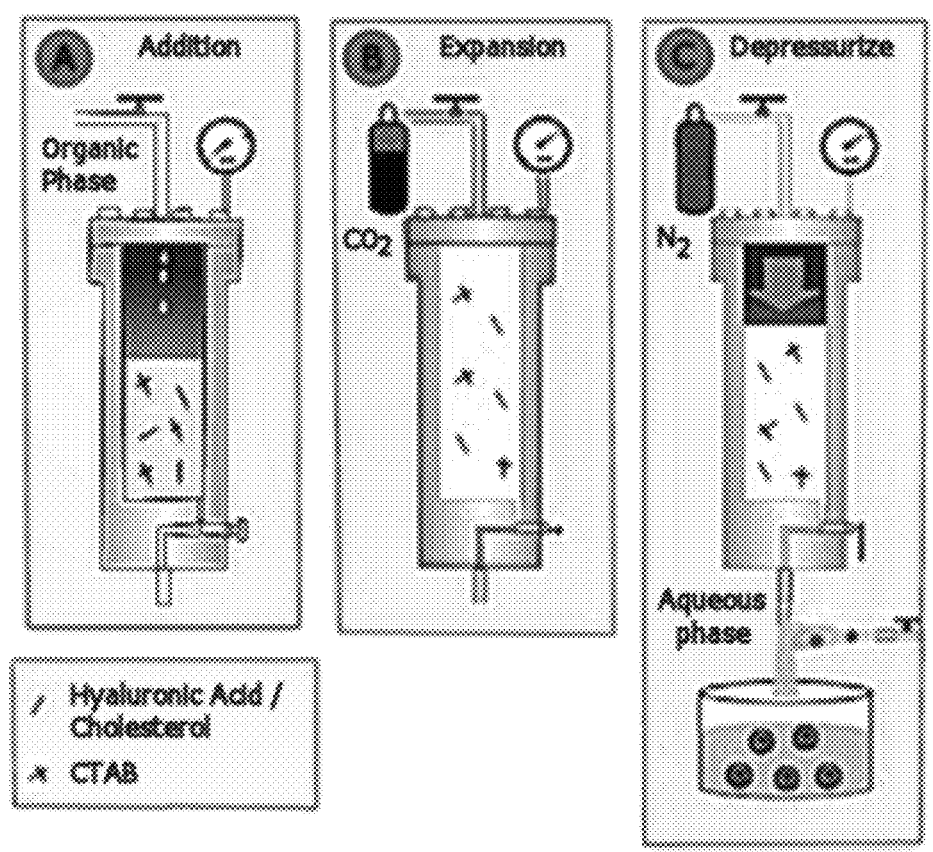
Figure 8.0

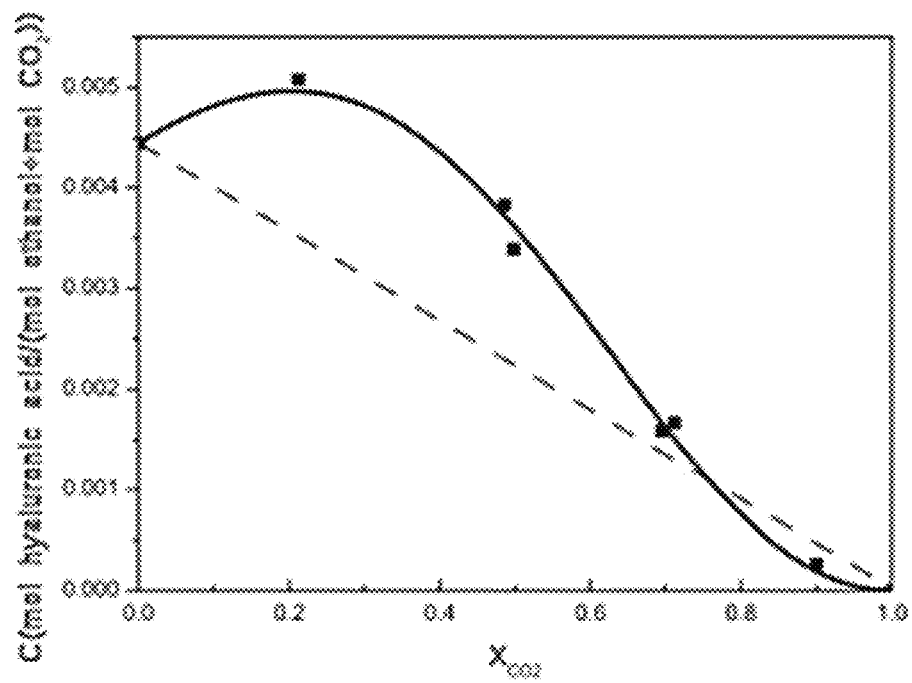
Figure 9.0
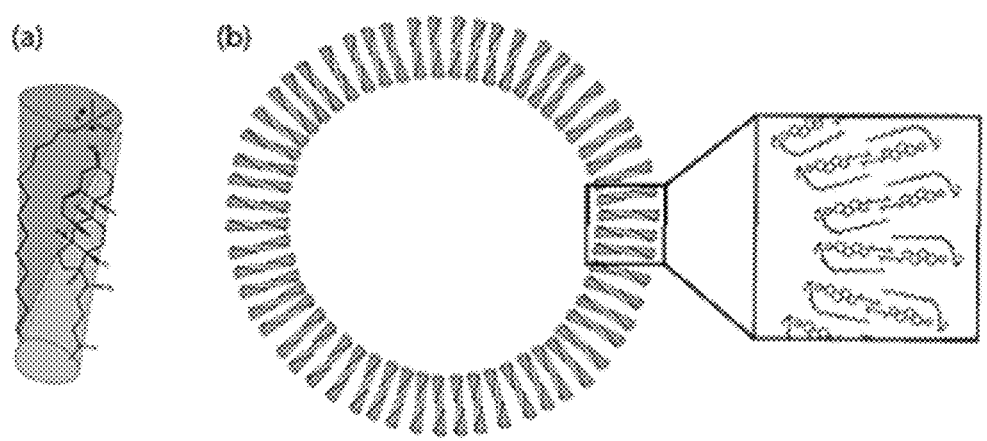
Figure 10.0

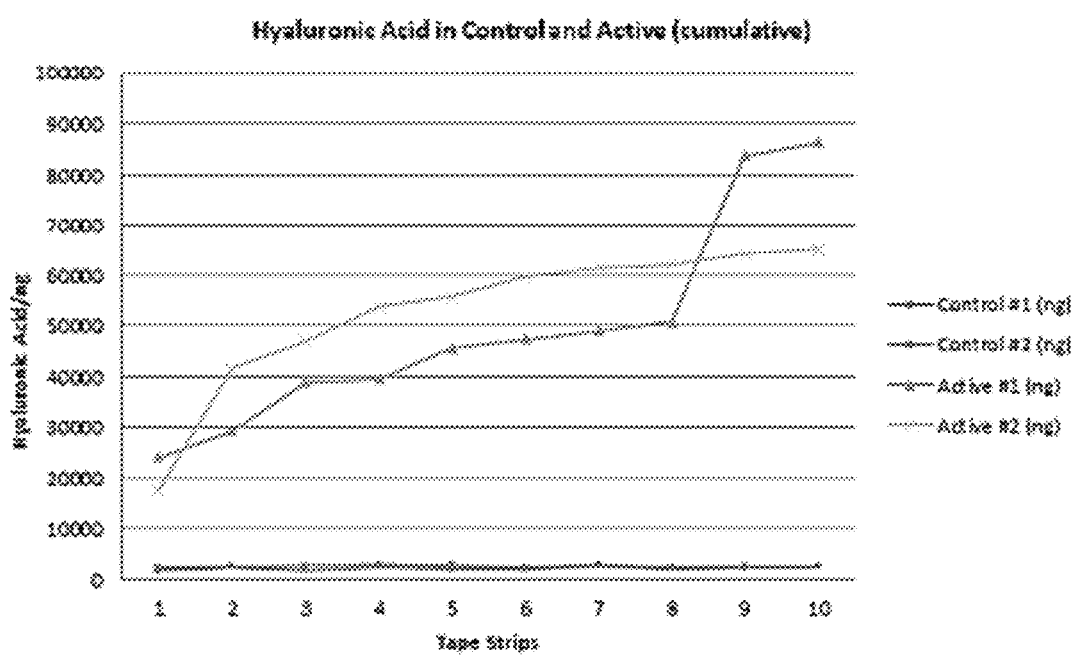
Figure 11.0

APPARATUS AND METHOD FOR PREPARING COSMECEUTICAL INGREDIENTS CONTAINING EPI-DERMAL DELIVERY MECHANISMS

PRIORITY APPLICATION

This is a continuation patent application drawing priority from U.S. patent application Ser. No. 14/971,320; filed Dec. 16, 2015. This present patent application draws priority from the referenced patent application. The entire disclosure of the referenced patent application is considered part of the disclosure of the present application and is hereby incorporated by reference herein in its entirety.

TECHNICAL FIELD

The application of innovative micro and nano vesicle forming technologies to effect beneficial results through the application of synthetic and natural ingredients to the skin has shown a great potential to significantly benefit the cosmetic formulation practice, offering solutions to many of the current limitations in ingredients, treatment style and management of human skin effected by environmental and physiological impact.

BACKGROUND

A liposome vesicle encapsulates a region of aqueous solution inside a hydrophobic membrane; dissolved hydrophilic solutes cannot readily pass through the lipids. Hydrophobic chemicals can be dissolved into the membrane, and in this way liposome can carry both hydrophobic molecules and hydrophilic molecules.

Several CFs (Compressed Fluid) methodologies have been used to generate vesicles, some of them already existed and others were developed for this specific application. Most of the methods involve a mixture between the compressed $CO_2$, the vesicle membrane constituents and an organic solvent for producing the vesicles upon contact with an aqueous phase.

Depending on the role of the compressed $CO_2$ used in each method, they can be classified as: Process involving the use of $CO_2$ as a solvent (e.g. Supercritical Liposome Method and Rapid Expansion of Supercritical Solutions), Processes involving the use of $CO_2$ as an antisolvent (e.g. Gas Antisolvent Precipitation and Aerosol Solvent Extraction System) and Processes involving the use of $CO_2$ as a co-solvent or a processing aid (e.g. Depressurization of an Expanded Liquid Organic Solution-Suspension and Supercritical Reverse Phase Evaporation).

Model hydrophilic and hydrophobic compounds, such as fluorescent dyes, sugars and cholesterol, have been encapsulated into vesicles using these methodologies whereas biomolecules like proteins, anticancer drugs and antibiotic, have been integrated in less extent.

Transdermal delivery systems (TDS) were introduced onto the US market in the late 1970s, but transdermal delivery of drugs had been around for a very long time. There have been previous reports about the use of mustard plasters to alleviate chest congestion and belladonna plasters used as analgesics. The mustard plasters were homemade as well as available commercially where mustard seeds were ground and mixed with water to form a paste, which was in turn used to form a dispersion type of delivery system.

Once applied to the skin, enzymes activated by body heat led to the formation of an active ingredient (allyl isothiocyanate). Transport of the active drug component took place by passive diffusion across the skin—the very basis of transdermal drug delivery.

The epi-dermis undergoes changes in structure and function which result in many of the characteristics of aged skin, including loss of elasticity, formation of wrinkles, loss of water-holding capacity, sagging, and poor microcirculation. At the molecular level, these changes have been correlated with biochemical changes in the content and structure of the extracellular matrix to which the major cells of the epi-dermis (i.e., the fibroblasts) reside. Collagen becomes highly cross-linked and inelastic, elastin is reduced in amounts and is incorrectly distributed, which results in reduced intercellular water for reduction and repair of these changes. Non-surgical options include chemical peels and chemicals with minor irritant properties (e.g., topical retinoid, salicylic acid, and alpha-hydroxy acids), are based on the principle of wounding the stratum corneum—the skin's primary defense against the transit of exogenous materials into the epidermis and dermis—to allow the penetration of constituents through the disrupted skin, which stimulates the desired response, typically restorative healing. All of these techniques require a wound healing response to the skins being intentionally wounded as a method to initiate the rejuvenation process.

Owing to the selective nature of the skin barrier, only a small pool of ingredients can be delivered non-systemically or systemically at therapeutically relevant rates. Besides great potency, the physicochemical ingredient characteristics often evoked as favorable for percutaneous delivery include moderate lipophilicity and low-molecular-weight. However, a large number of skin damage mitigating active agents do not fulfill these criteria.

Chemical permeation enhancers facilitate drug permeation across the skin by increasing drug partitioning into the barrier domain of the stratum corneum, increasing drug diffusivity in the barrier domain of the stratum corneum or the combination of both (2).

The heterogeneous stratum corneum is composed of keratin 'bricks' and intercellular continuous lipid 'mortar' organized in multilamellar strata (3)(4)(5). Depending on the nature of the drug or ingredient, either of these two environments may be the rate-limiting milieu (barrier domain) for the percutaneous transport.

As a consequence, it is anticipated that the magnitude of permeation improvement obtained with a given permeation enhancer will vary between lipophilic and hydrophilic ingredients. Several mechanisms of action are known: increasing fluidity of stratum corneum lipid bilayers, extraction of intercellular lipids, increase of ingredient's thermodynamic activity, increase in stratum corneum hydration, alteration of proteinaceous corneocyte components and others.

The stratum corneum is a formidable barrier to exogenous agents including cosmeceutical ingredients. Therefore, it is often necessary to add permeation-enhancing chemicals to aid beneficial constituents in passing through the stratum corneum. Permeation-enhancing chemicals include fatty acids, organic solvents (i.e., acetone and ethanol), alcohols, esters and surfactants.

It is generally understood that for enhancers, increased potency is directly correlated with increased skin irritation. Difficulty in reducing the irritation of these agents has been expressed since the same mechanisms responsible for increasing permeation cause irritation. While potent enhancers are effective at transiently compromising the integrity of the stratum corneum barrier, their action is not entirely limited to the stratum corneum and the interaction with viable epidermis can cause cytotoxicity and irritation. Published methods for reducing the skin irritation of permeation enhancers include combining permeation enhancers (synergistic mixtures) and manipulation of their chemical structures.

Conventional lipid or niosome vesicle production techniques have drawbacks such as complex and time consuming procedures involving organic solvents. For liposomes, conventional methods can involve harsh conditions that result in denaturation of the lipids and active ingredients, and also cause poor ingredient encapsulation efficiency.

Since the liposomes were first used as drug carriers in 1970s. Many methods, such as Supercritical fluids (SCFs), for preparing liposomes have been developed, but these methods require large amounts of organic solvents like chloroform, ether, freon, methylenechloride and methanol that are harmful to the environment and the human body, and very few methods have been developed that yield liposomes that have a high trapping efficiency for water soluble substances without using any organic solvent.

Additionally, all these methods are not suitable for mass production of liposomes because they consist of many steps. With the advent of Green Chemistry in the early 1990s, the surge of supercritical fluids (SCFs) increased vastly.

The supercritical state of a fluid (SCF) is intermediate between that of gas and liquids. The SCF has been used widely in pharmaceutical industrial operations including crystallization, particle size reduction, drug delivery preparation, coating and product sterilization. In the pharmaceutical field, supercritical carbon dioxide (scCO2) is by far the most commonly used gas, which can become supercritical at conditions that are equal or exceed its critical temperature of 31.1° C. and its critical pressure of 7.38 Megapascals (Mpa).

The encapsulation degree of any drug into vesicles is influenced by several parameters related to the: a) vesicle composition, b) the nature of the cosmeceutical ingredient and c) the preparation methodology. Regarding the vesicle composition, besides the selection of the lipids forming the membrane and the presence of charges on it, the type of vesicle plays also an important role. Thus, for hydrophilic drugs, such as proteins or peptides, the encapsulation degree appears to increase in the following order: MLV<SUV<LUV. (FIG. 1.0) Nevertheless in the case of hydrophobic drugs, the size and type of liposomes do not seem to play a major role.

Liposomes with a single bilayer are known as unilamellar vesicles (UV). UVs may be made extremely small (SUVs) or large (LUVs) (FIG. 3.0). Liposomes are prepared in the laboratory by sonication, detergent dialysis, ethanol injection, French press extrusion, ether infusion, and reverse phase evaporation.

These methods often leave residuals such as detergents or organics with the final liposome. From a production standpoint, it is clearly preferable to utilize procedures which do not use organic solvents since these materials must be subsequently removed.

Some of the methods impose harsh or extreme conditions which can result in the denaturation of the phospholipid raw material and encapsulated ingredients. These methods are not readily scalable for mass production of large volumes of liposomes.

Several methods, such as energy input in the form of sonic energy (sonication) or mechanical energy (extrusion), exist for producing MLVs (multilamellar vesicles), LUVs and SUVs without the use of organic solvents.

MLVs (multilamellar vesicles), free of organic solvents, are usually prepared by agitating lipids in the presence of water. The MLVs are then subjected to several cycles of freeze thawing in order to increase the trapping efficiencies for water soluble ingredients.

MLVs are also used as the starting materials for LUV and SUV production. One approach of creating LUVs, free of organic solvents, involves the high pressure extrusion of MLVs through polycarbonate filters of controlled pore size. SUVs can be produced from MLVs by sonication, French press or high pressure homogenization techniques. High pressure homogenization has certain limitations. High pressure homogenization is useful only for the formation of SUVs. In addition, high pressure homogenization may create excessively high temperatures.

Contrary to the present embodiment, extremely high pressures are associated with equipment failures. High pressure homogenization does not insure end product sterility. High pressure homogenization is associated with poor operability because of valve plugging and poor solution recycling.

The use of liposomes for the delivery and controlled release of therapeutic drugs requires relatively large supplies of liposomes suitable for in vivo use (FIG. 6.0). Present laboratory scale methods lack reproducibility, in terms of quantity and quality of encapsulated ingredients, lipid content and integrity, and liposome size distribution and captured volume.

The multidimensional characteristics of the ingredient and the liposome, as well as potential raw material variability, influence reproducibility. Present state-of-the-art liposome and niosome products are not stable. It is desirable to have final formulations which are stable for six months to two years at room temperature or at refrigeration temperature.

Present liposome products are difficult to sterilize. Sterility is currently accomplished by independently sterilizing the component parts lipid, buffer, ingredient and watery autoclave or filtration and then mixing in a sterile environment.

This sterilization process is difficult, time consuming and expensive since the product must be demonstratively sterile after several processing steps. Heat sterilization of the finished product is not possible since heating liposomes or niosomes does irreparable damage. Filtration through 0.22 micron filters may also alter the features of multilayered liposomes and elastic niosomes.

Gamma ray treatment, not commonly used in the pharmaceutical industry, may disrupt liposome or elastic niosome membranes. Picosecond laser sterilization is still experimental and has not yet been applied to the sterilization of any commercial pharmaceutical.

In the past two decades, several cosmetic formulations based on ingredient delivery systems have been successfully introduced for the treatment of skin disorders. Many problems exhibited by free active cosmetic ingredients (ACIs), such as poor solubility, toxicity, rapid in vivo breakdown, unfavorable pharmacokinetics, poor bio distribution and lack of selectivity for target tissues can be ameliorated by the use of a VDS (vesicle delivery system) as offered by the current embodiment. Although a whole range of delivery agents exist nowadays, the main components typically include a nanocarrier, a targeting moiety conjugated to the nanocarrier, and a cargo, such as the desired cosmeceutical ingredient.

In 1846, Gobley separated phospholipids from egg yolk. The term "lecithin" which is derived from the Greek lekithos was first used to describe a sticky orange material isolated from egg yolk. "Lecithin" refers to the lipids containing phosphorus isolated from eggs and brains; (3) from a scientific point of view, "lecithin" refers to PCs (phosphatidylcholine) the most common phospholipid, egg yolks, liver, wheat germ and peanuts contain the phospholipid lecithin.

Phospholipids (FIG. 3.0) have excellent biocompatibility. In addition, phospholipids are renowned for their amphiphilic structures. The amphiphilicity confers phospholipids with self-assembly, emulsifying and wetting characteristics. When introduced into aqueous milieu, phospholipids self-assembly generates different super molecular structures which are dependent on their specific properties and conditions.

In the need for synthetic analogs of natural phospholipids, further synthetic phospholipids were for instance designed to optimize the targeting properties of liposomes. Examples are the PEG-ylated phospholipids and the cationic phospholipid 1,2-diacyl-P-O ethylphosphatidylcholine. Also attempts were made to convert by organic chemical means phospholipids into pharmacological active molecules (for instance ether phospholipids or to make phospholipid pro-drugs.

DPPC is the major constituent of stratum corneum surfactants which controls the dynamic surface tension (DST) and helps maintaining the epi-dermis health. It is also one of the most popular phospholipids used for preparing lipid or niosome bilayers and model biological membranes.

SUMMARY

The present embodiment features methods and apparatus for producing liposomes and niosomes containing hydrophobic and hydrophilic ingredients know to be beneficial to the repair and rejuvenation to the stratum corneum and underlying epi-dermis with the ability to effect non-systemic drug absorption and transportation are influenced by various factors. The methods and apparatus are suitable for large scale production of pharmaceutical grade liposomes which are sterile, of a predetermined size, and are substantially free of organic solvents. The present embodiment features a method of making liposomes and elastic niosomes using low pressure fluids.

As constructed according to the present embodiment example, nano and macro carriers can be either unimolecular (i.e.: dendrimers, carbon nanotubes, polymer-conjugate drug/protein, etc.) or multimolecular carries, based on molecular self-assemblies (nanoshells, vesicles, etc.). Their major constituents are either lipids or polymers and they all have in common that the final arrangement is governed by the nature of the initial components and the methodology used in their preparation. Some of the advantages are the incorporation of ACIs (active cosmeceutical ingredients).

One method of the example embodiment comprises the steps of forming a solution or mixture of a phospholipid, a hydrophobic or hydrophilic cosmeceutical ingredient, an aqueous phase and a low pressure fluid. The solution or mixture is decompressed to separate the low pressure, critical fluid, from the phospholipid and aqueous medium, to form one or more liposomes. This method is referred to as the decompression method of forming liposomes in the embodiment. Preferably, the rate of depressurization influences the size of the liposomes formed.

According to the procedure of the example embodiment, schematically represented in FIG. 4.0, operating always under mild conditions to preserve the activity of the labile biomolecules. The general method consists in loading a solution of the membrane lipid components and the desired hydrophobic bio-actives in an organic solvent (e.g. ethanol), into the high-pressure reactor previously driven to the preferred working temperature (FIG. 4.0 A). The reactor is then pressurized, in a second stage, with a large amount of compressed CO2 until reaching the working pressure (10 MPa) (FIG. 4.0 B).

Finally in the third stage, the vesicular conjugates are formed by depressurizing the resulting CO2-expanded solution over an aqueous phase, which might contain water soluble surfactants and hydrophilic bio-actives (FIG. 4.0 C). In this step a flow of N2 at the working pressure is used in order to push down the CO2-expanded solution and to keep constant the pressure inside the reactor. It is worth to note that no further energy input is required for achieving the desired SUVs (small unilamellar vesicles) structural characteristics, neither for increasing the loading or functionalization.

In applications utilizing the example embodiment with low pressure fluids, the properties of the coating material and particularly the interactions of coating materials with low pressure low temperature fluids are especially important.

These interactions may be important for enabling the incorporation of cosmeceutical essential oils into carrier materials, for example by facilitating the diffusion of the essential oil due to the swelling and opening of the pores of carrier material particles.

One method comprises the steps of (1) forming a solution or mixture of a phospholipid, (2) an aqueous phase and low pressure low temperature methodologies. (3) The solution or mixture is decompressed to separate the fluid, from the phospholipid and aqueous media, to form one or more liposomes.

In some embodiments, the aqueous, or addition phase, has a therapeutic cosmeceutical agent included. As used herein, the term "therapeutic cosmeceutical agent" means a chemical or ingredient capable of effecting a desirable response in an individual subject. This embodiment is ideally suited for therapeutic cosmeceutical agents which are not shear sensitive.

Preferably the compressed fluid is recycled. To the extent that phospholipids and aqueous phase are carried over with the CF, such components may also be recycled. For convenience, liposomes formed with CF fluid in the current embodiment are referred to as "LPLTVs."

An example embodiment features an apparatus for forming liposomes/niosomes (non-ionic) vesicles. The apparatus comprises a first vessel wherein a phospholipid, an aqueous phase and a CF are combined to form a mixture or solution. The apparatus further comprises a second vessel in communication with the first vessel for expansion.

The apparatus of the embodiment further comprises a third vessel for depressurization as a means capable of reducing the pressure of the solution or mixture. Depressurization means may be interposed between the first and second vessels or may be integral with a third vessel. The third vessel receives the solution or mixture of phospholipids and an aqueous phase which form liposomes upon depressurization.

Preferably, the CF is removed from depressurization means and/or the third vessel and recycled.

One example embodiment comprises the steps of forming a solution or mixture of a phospholipid and a compressed fluid. The solution or mixture is then decompressed through a tip or orifice into an aqueous phase to form one or more liposomes. As a result of the decompression, the CF is separated from the phospholipids and the aqueous phase.

The released CF is either vented or recycled to form a solution or mixture of phospholipid.

A further example embodiment features a method of making liposomes or niosomes comprising the steps of forming a solution or mixture of a phospholipid and a CF. The solution or mixture is injected into an aqueous phase to form one or more liposomes or niosomes as the phospholipids and CFs are decompressed.

Preferably, the aqueous phase or phospholipids contain a cosmeceutical therapeutic agent which is incorporated into the liposome or niosomes.

Embodments of the present method are ideally suited for skin rejuvenating agents which are shear sensitive such as botanicals, proteins and peptides. Embodiments of the present method do not subject botanicals, proteins and peptides to extreme shear forces or temperatures.

Example embodiments are ideally suited to form unilamellar liposome or niosome vesicles. The size of the liposome or niosome is determined by the rate of decompression.

A preferred method uses a CF selected from the group of compositions capable of forming a critical fluid comprising carbon dioxide; nitrous oxide; halo-hydrocarbons, such as FREON; alkanes such as propane and ethane; and alkanes such as ethylene.

One example embodiment features an apparatus for forming liposomes and niosomes. The apparatus comprises a first vessel for containing a solution or mixture of a phospholipid and a compressed fluid. The apparatus further comprises a second vessel for containing an aqueous phase. The first vessel and the second vessel are in communication by means of injection means for injecting the phospholipid and CF fluid mixture into the aqueous phase. Upon injection into the aqueous phase in the third vessel, liposomes are formed.

Preferably, the aqueous phase contains a cosmeceutically therapeutic agent which cosmeceutical therapeutic agent is encapsulated within the liposome.

Conjugation of cosmeceutical bio-beneficial ingredients to nano carriers can offer over the free ingredient the protection from premature degradation, a higher stability, an enhance permeability through biological membranes, a higher control of the pharmacokinetics, a better ingredient tissue distribution profile, and an improvement of intracellular, intercellular, and intra-follicular penetration and the ability to control whether the nano-carrier goes systemic or non-systemic.

BRIEF DESCRIPTION OF THE DRAWINGS

For a better understanding of the example embodiments, reference should be made to the following detailed description disclosed in conjunction with the accompanying drawings, in which:

FIG. 1.0 illustrates the classification of vesicles regarding size and lamellarity.

FIG. 2.0 illustrates the construction and composition of phospholipids

FIG. 3.0 illustrates the major classifications of liposomes as vesicular systems according to their size and membrane lamellarity.

FIG. 4.0 (A, B, C) is a representation of the steps of forming a solution or mixture of a phospholipid, an aqueous phase and low pressure low temperature methodologies.

FIG. 5.0 is a TEM image of liposomes produced in the LPLTVs process.

FIG. 6.0 is an image of the appearance of small spheres aggregating into larger spheres or captured within larger spheres in the LPLTVs liposomal forming process.

FIG. 7.0 shows rod or coffee-bean morphology observed in the liposomes samples produced by the LPLTVs process.

FIG. 8.0 is a schematic representation of the LPLTV process method.

FIG. 9.0 shows a solubility curve of hyaluronic acid and cholesterol, in ethanol/CO2 at 10 MPa and 308 K.

FIG. 10.0 is a schematic illustration of the formation of (a) the hyaluronic acid cholesterol/CTAB bimolecular amphiphile and (b) their self-assembling into bilayer vesicles based on the packing parameter concept.

FIG. 11.0 is a chart showing Hyaluronic Acid levels in active and control samples.

DETAILED DESCRIPTION

The present embodiment features methods and apparatus for producing cosmeceutically benevolent ingredient content liposomes and niosomes. The methods and apparatus are suitable for large scale production of pharmaceutical and cosmeceutical grade vesicles for the treatment of skin anomalies created as a result of aging skin or chronic environmental insult which are sterile, of a predetermined size, and are substantially free of organic solvents.

Definitions

As used herein, the word "hydrophilic" in relation to the material means that that material is above 10% soluble in water by weight at standard temperature and pressure (STP).

As used herein, the word "hydrophobic" as used in relation to a material means that that material is less than 0.1% soluble in water by weight at standard temperature and pressure (STP).

As used herein, the term (IDS) as used in relation to the explanation of the current embodiment means Ingredient Delivery Systems.

As used herein, the word "micelle" as used in relation to a material means "molecules having both polar or charged groups and non-polar regions (amphiphilic molecules) formed aggregates".

As used herein, the word "vesicle" as used in relation to one prepared artificially, in which case they are called liposomes. If there is only one phospholipid bilayer, they are called unilamellar liposome vesicles; otherwise they are called multilamellar.

As used herein, the word "niosome" as used in relation to a non-ionic surfactant-based Vesicle formed mostly by non-ionic surfactant and cholesterol incorporation as an excipient.

As used herein, the term "LPLTVs as used means Low Pressure Low Temperature alternative construction of Vesicles based on milder conditions of pressure (<10 MPa) and temperature (<308 K) than the previously described methodologies based on CFs (Compressed Fluids).

As used herein, the term Active Cosmetic Ingredients (ACIs) as used means but is not limited to such substances as synthetic or natural skin rejuvenating ingredients, sunscreen ingredients, skin-lightening agents, and anti-acne ingredients.

As used herein, the term CFs as used means such substances made from compressed fluids based technologies to produce niosomes or vesicles.

As used herein, the term phospholipids as used means lipids containing phosphorus, a polar potion and non-polar potion in their structures.

As used herein, the term niosomes are microscopic lamellar vesicular structures, which are formed on the admixture of non-ionic surfactant and cholesterol with subsequent hydration in aqueous media.

One example embodiment features an apparatus for forming liposomes and niosomes. The apparatus comprises a first vessel or mixing the organic phase, a second vessel for containing a mixture of multi-lamellar vesicles and a compressed fluid and a third vessel for decompressing into the aqueous phase. The first vessel is in communication with a second vessel which second vessel is in communication with a third vessel capable of decompressing the mixture to remove the compressed fluid. During decompression, one or more liposomes or niosomes are formed.

Another embodiment further comprises a third vessel for forming multilamellar vesicles by hydrating phospholipids in an aqueous phase.

In the embodiment, the aqueous phase or the phospholipids may contain a therapeutic agent to impart special qualities to the liposome for beneficial partitioning of the stratum corneum to aid in transiting cosmeceutically beneficial liposomes or niosomes to the epi-dermis.

An embodiment further features control means for determining the rate of decompression. The rate of decompression determines the size of liposomes or niosomes.

Preferably, compressed fluid removed from the liposome preparation in the decompression vessel is recycled to the first vessel to form additional mixtures of multilamellar vesicles and compressed fluid.

Contact with compressed fluid may cause destruction of the cellular structures particularly upon rapid decompression. Thus, embodiments are, for the most part, self-sterilizing.

Methods and apparatus of the example embodiment are capable of forming liposomes or niosomes which carry a cosmeceutical therapeutic agent. The cosmeceutical therapeutic agent can be incorporated into ingredients which are used to form the liposome or niosome or the liposome or niosome can be loaded with the cosmeceutical therapeutic agent after the liposome or niosome is formed.

Embodiments allow the recovery of raw materials, lipids and solvents which are not incorporated into the final liposome or niosome product. Example embodiments feature efficient cosmeceutical ingredient entrapment and recovery of un-encapsulated cosmeceutical ingredient. The operating parameters of the apparatus and method are consistent with other industrially applied processes. The method and apparatus are capable of operating continuously.

These and other features, aspects, and advantages of the embodiment will become evident to those of ordinary skill in the art from a reading of the present disclosure.

During the depressurization step of the example embodiment, the expanded organic solution experiences a large, abrupt and extremely homogenous temperature decrease produced by the $CO_2$ evaporation from the expanded solution. This is the reason that explains the obtaining of homogenous vesicles regarding size, lamellarity and morphology compared with the same system but prepared by a conventional mixing method.

However, changes in the procedures and equipment, as in the present embodiment, result in vesicular systems with differentiated characteristics. The processes can also be distinguished by the latter hydration step that can occur either during the pressurization or the depressurization step.

These lipid or niosome vesicles of the present embodiment allow the physicochemical properties of ingredient molecules, of a higher molecular weight in excess of 700 kDa, in a liposomal system to be changed, which facilitates crossing of the stratum corneum barrier into the epi-dermis.

The size of the liposome can be controlled by the rate of decompression to form liposomes or niosomes of predetermined size to control the volume and depth of penetration.

Among the various approaches for exploiting developments in nano and micro technology for cosmetic applications, ingredient delivery systems (IDS) have already had an enormous impact on cosmetic formulation technology, improving the performance of many existing ingredients and enabling the use of entirely new therapies. The fact that IDSs can protect sensitive molecules, such as hormones, enzymes and proteins, from degradation and the in-vivo attack of the immune system providing longer resident times, have been used to improve the effectiveness and delivery of these ingredients. Although nano and micro particulate carriers can be made from a variety of organic and inorganic materials, vesicle and polymer based-nanocarriers are perhaps the most widely used for ingredient delivery purposes.

Particularly vesicles, liposome and noisome, have served as convenient delivery vehicles for biologically active compounds because they are non-toxic, biodegradable and non-immunogenic. Contrary to products where the active substance is in simple solution, the pharmacological properties of vesicle-based delivery systems strongly depend on the structural characteristics of the conjugates. Indeed, a high degree of structural homogeneity regarding size, morphology and vesicle organization in the membrane is crucial, for their optimum performance as functional entities.

Liposomes and niosomes are vesicles in which, in the current embodiment, cosmeceutical ingredients can be trapped and administered more efficiently. However, these vesicles, micelle, liposome and niosome, are not similar to each other. In a comparison, micelles vs. liposomes, and or elastic niosomes, the differences between the two are explained as; Micelles are structures composed of a monolayer of amphipathic molecules. In a biological system, the molecules tend to arrange themselves in such a manner that the inner core of these structures are hydrophobic and the outer layers are hydrophilic in nature.

Liposomes as in the present embodiment, are composed of a bilayer of amphipathic molecules, the molecules are arranged in two concentric circles, such that the hydrophilic heads of the outer layer are exposed to the outer environment, and the hydrophilic heads of the inner layer make the inner hydrophilic core. The hydrophobic tails are tucked between the two layers.

In the present embodiment, elastic liposomes are microscopic vesicles having single or multiple phospholipid bilayers which can entrap hydrophilic compounds within their aqueous cores.

Elastic niosomes are composed of nonionic surfactants, ethanol and water. They are superior to conventional niosomes because they enhance penetration of a drug through intact skin by passing through pores in the stratum corneum, which are smaller than the vesicles. In fact, their elasticity allows them to pass through channels that are less than one tenth of their own diameter. Thus they can deliver ingredients or compounds of both low and high molecular weight. Furthermore, they can provide prolonged action and demonstrate superior biological activity compared to conventional niosomes. The transport of these elastic vesicles is concentration independent and driven by trans-epidermal hydration.

To deliver the molecules to sites of action, the lipid or niosome bilayer can fuse with other bilayers such as the cell membrane, thus delivering the liposome contents. By making liposomes in a solution of natural or synthetic ingredients that can effect a beneficial change to the skin, (which would normally be unable to diffuse through the membrane) they can be (indiscriminately) delivered past the lipid bilayer. A liposome or niosome vesicle does not necessarily have lipophobic contents, such as water, although, in the case of the present embodiment, it usually does.

The preferred phospholipid in the current process embodiment is naturally derived, for example phospholipids obtained from plant or animal sources. Natural phospholipids are purified from, e.g., soybean, rapeseed, and sunflower seed. The phospholipid may be salted or desalted, hydrogenated or partially hydrogenated or natural, semi-synthetic or synthetic.

Liposomes, niosomes and in general vesicles, are undoubtedly one of the most promising carriers in nano and micro cosmeceutical ingredient delivery. They are particularly important in the stratum corneum percutaneous transit field due to their great versatility respect to size, composition, surface characteristics, biocompatibility, biodegradability, low toxicity, capacity for entrapping and/or integrating hydrophilic and/or hydrophobic molecules and possibility of surface functionalization. Vesicles of the present process embodiment are spherical objects enclosing a liquid compartment, with a diameter ranging from 20 nm to a few thousand of nanometers, separated from its surroundings by at least one thin membrane consisting of a bilayer (unilamellar) or several layers (multilamellar) of amphiphilic molecules.

Sometimes the terms liposome, niosome and vesicle are used interchangeably, although a liposome is a type of vesicle composed mainly by phospholipids, a niosome as a non-ionic surfactant-based vesicle formed mostly by non-ionic surfactant and cholesterol incorporation as an excipient. Vesicles can be formed also by non-lipid building blocks, such as block co-polymers or cationic or non-ionic surfactants.

A liposome or niosome is an artificially-prepared vesicle composed of a lipid bilayer. The liposome or niosome can be used as a vehicle for administration of percutaneous skin nutrients and pharmaceutical drugs. Liposomes and niosomes are composed of natural phospholipids, and may also contain mixed lipid chains with surfactant properties (e.g., egg phosphatidylethanolamine). According to the present process embodiment, a liposome design may employ surface ligands for attaching to unhealthy tissue.

In the present embodiment, phospholipids have a propensity to form liposomes and niosomes, which can be employed as the cosmetic ingredient carriers. Phospholipids have good emulsifying property which can stabilize the cosmetic serum emulsions. In addition, phospholipids as surface-active wetting agents which can coat on the surface of crystals to enhance the hydrophilicity of hydrophobic ingredients. The above properties are successfully employed in the LPLTVs design.

As used herein, in the current embodiment example, the term "phospholipid" refers to compositions which are esters of fatty acids in which the alcohol component of the molecule contains a phosphate group as an integral part (FIG. 2.0).

In order to extend LPLTVs (Low Pressure Low Temperature alternative construction of Vesicles) to the preparation of other kinds of vesicle systems taking full advantage of the possibilities offered by this process were also undertaken. Phospholipids-based formulations are widely used for delivery purposes and for this reason 1,2-dipalmitoyl-sn-glycero-3-phosphocholine (DPPC) was selected as a membrane component for the liposome preparation with LPLTVs.

Phospholipids comprise the glycerol-phosphatides, containing glycerol, and the sphingomyelins containing sphingosine.

According to the alcohols contained in the phospholipids, they can be divided into glycerophospholipids and sphingomyelins.

For the present embodiment, the use of Glycerophospholipids, which are the main phospholipids in eukaryotic cells, refer to the phospholipids in which glycerol is the backbone are preferred. All naturally occurring glycerophospholipids possess α-structure and L-configuration.

Preferred phospholipids used in the embodiment comprise phosphatidylcholine, phosphatidylethanolamine, phosphatidylserine and sphingomyelin; and although not preferred, in the present embodiment, synthetic phospholipids comprising dimyristoyl phosphatidylcholine, dipalmitoyl phosphatidylcholine, distearoyl phosphatidylcholine, distearoyl phosphatidylglycerol, dipalmitoyl phosphatidylglycerol, dimyristoyl phosphatidylserine, distearoyl phosphatidylserine, and dipalmitoyl serine.

In the case of the present method embodiment, liposomes or niosomes are used as carriers for beneficial ingredients for the treatment of skin anomalies. Liposomes and niosomes can be made with different features can enhance an ingredients efficacy, reduce an ingredients toxicity, restriction from going systemic and prolong the ingredients therapeutic effect.

Niosomes are self-assembled vesicles composed primarily of synthetic surfactants and cholesterol. They are analogous in structure to the more widely studied liposomes formed from biologically derived phospholipids.

The type of epi-dermal activity resulting from the application of the current embodiment's content of natural or synthetic ingredients to be beneficial includes: Hydration •Skin lightening •Anti-wrinkle/skin smoothing •Antioxidant activity/free radical scavenger •Anti-inflammatory/anti-irritant •Collagen stimulation •Cell regeneration/stimulation •Sebum regulation •Anti-cellulite •Antimicrobial •Antibacterial.

With chronological age and chronic exposure to adverse environmental factors, (notably UVA, UVB, and IR radiation) the visual appearance, physical properties, and physiological functions of skin change in ways that are considered cosmetically undesirable. The most notable and obvious changes include the development of fine lines and wrinkles, loss of elasticity, increased sagging, loss of firmness, loss of color evenness (tone), coarse surface texture, and mottled pigmentation.

Less obvious, but measurable changes which occur as skin ages or endures chronic environmental insult include a general reduction in cellular and tissue vitality, reduction in cell replication rates, reduced cutaneous blood flow, reduced moisture content, accumulated errors in structure and function, and a reduction in the skin's ability to remodel and repair itself.

Many of the above alterations in appearance and function are caused by changes in the outer epidermal layer of the skin, while others are caused by changes in the lower dermis.

Regardless of the stimulus for skin damage, when damage occurs, numerous natural and complex biochemical mechanisms are set into motion in attempts to repair the damage.

The present embodiment relates generally to construct a process for a vesicle-driven treatment method and composition for improving the skin's visual appearance, function, and clinical/biophysical properties which have been changed by factors such as chronological age, chronic sun exposure, adverse environmental pollutants, household chemicals, disease pathologies, smoking, and malnutrition. In particular, the present embodiment relates to a process to create a method of treating skin by increasing the skin's stratum corneum transit of known beneficial ingredients through dynamic infusion of vesicles (DIV) generated from natural and biocompatible phospholipids with an aqueous volume enclosed within a lipid or niosome membrane.

The result of the present process embodiment is to deliver larger molecular weight, longer lasting, beneficial ingredients to areas of the epi-dermis depleted of needed vitamins, hydration, nourishment and complimentary ingredients need for the rejuvenation of elastin and collagen.

Now, in the current embodiment, comes the development of a new, single process, ingredient vesicle methodology based on a Low Pressure Low Temperature alternative construction of liposome or niosome Vesicles process (LPLTVs) for the direct, robust and scalable encapsulation of biomolecules in vesicles. The development of reproducible and scalable methodologies in order to functionalize those vesicles with targeting/protective units enabling greater selectivity of the therapeutic epidermal targets and therefore more effective treatments.

The use of the biomolecules-vesicles conjugates prepared by LPLTVs can be used in the treatment of different skin anomalies. The embodiments process uses milder conditions of pressure (<10 MPa) and temperature (<308 K) than previous methodologies based on CFs, allowing the processing of heat labile compounds and reducing the investment cost of a high pressure plant when the process is scaled-up.

The present embodiment encompasses compressed fluid-based methodologies (CF), also called dense gas technologies, for the production of lipid-based ingredient carrier systems with structural characteristics not reachable by already existing procedures using liquid organic solvents. In the present embodiment, we have improved the processing of vesicles and niosomes because they provide the ability to reduce the amount of organic solvent required by conventional methods and allow a better control over the final vesicle structural characteristics. Moreover compressed fluid processing offers sterile operating conditions and the ability for one-step production processes, which is convenient in transferring the technology to larger scale operations.

The present embodiment's compressed fluid technology was developed as a platform for producing lipid and niosome-based cosmetic ingredient carrier systems that can address most of the limitations of conventional methods.

LPLTVs methodology allows an easy and direct preparation of different liposome-biomolecule conjugates with micro and nano scopic sizes and great degrees of unilamelarity.

The stability time of the liposome-based conjugates is somewhat smaller than those of LPLT Vesicle-based conjugates. This stability is improved by the addition of stabilizing/targeting units to the formulation.

Bioactivity of the integrated biomolecules is unaffected under the processing conditions with CO2-expanded solvents.

Liposomes and Niosomes prepared by the current embodiment's process of LPLTVs, fulfill the structural and physio-chemical requirements to be a platform for the percutaneous delivery of synthetic or natural ACIs (active cosmeceutical ingredients).

Major advantages of the embodiment's application of CFs technology are that sterile and stable liposomal and niosomal formulations can be produced with minimum amounts of organic solvents.

In the case of blemished or compromised complexion of the skin the following properties could be desirable: •Sebum regulating •Anti-bacterial •Anti-inflammatory/anti-irritant •Soothing/calming •Skin healing and regeneration •uniform complexion •lightening and brightening.

These and other advantages will be apparent to individuals skilled in the art in view of the drawings and detailed description which follow.

Examples of some preferred preparation ingredients in the present embodiment include natural botanicals, those ingredients that that originates from plants, herbs, roots, flowers, fruits, leaves or seeds such as: aloe vera, almond oil, avocado oil, coconut oil, hazelnut oil, jojoba oil, olive oil, palm oil, pumpkin seed oil, sesame oil, sunflower oil, tamanu oil, candeia oil, arnica, chamomile, oat extract, hibiscus flower, boswellia serratta, cocoa powder, green and white tea, gotu kola, chamomile extract, L-arginine, glutamine, pantothenic acid, white willow bark extract, tetrahydrocurcuminoids, alpha-arbutin, aloesin, alpha glucosyl hesperidin, niacinimide, fucoidan, magnesium asorbyl phosphate, azelaic acid, N-acetyl-D-glucosamine, glutathione, mulberry, pomegranate seed oil, cyprus rotund root extract, licorice, licorice-glabrin root extract, kojic acid, panax ginseng root extract, ginko bilbao, salicylic acid, Lauric acid, glycerin, caffeine, tocopheryl acetate, copper peptide, retinyl palmitate, asorbyl palmitate, wakame, dimethylethanolamine, beta glucan, triglyceride as well as hyaluronic acid (Hyaluronic acid is a natural and sugar-like biopolymer in the human body that alternately consists of D-glucuronic acid and N-acetyl-D-glucosamine-units).

Additionally, preferred natural polymers for the current embodiment such as starch, starch, xanthan or guar gum, carrageenan, alginates, polysaccharides, pectin, gelatin, agar, and cellulose derivatives can be used to this end. On the synthetic side, polyacrylate derivatives and polyacrylamide polymers can be incorporated in to the carrier system of the present embodiment. More recent developments include combining hydrophobic and hydrophilic polymers into block and star copolymers and thermally responsive systems.

Polymers are particularly susceptible to the construction of vesicle that can physically entrap the active component, preserving its biological stability, or the bioactive component can be incorporated chemically into a polymer chain or pendant group, then released through hydrolysis. For example, salicylic acid (an anti-acne ingredient) can be incorporated into the main chain of polyanhydride ester and released within a short time.

The current example embodiment also applies to the construction of vesicle encapsulated polymers that are routinely used in many personal care and cosmetic products.

The current embodiment takes advantage of the various properties of these polymers to impart unique benefits to their formulations. The range of properties is as varied as the class of polymers that have been utilized. Using polymers, cosmetic chemists can create high performance products. Broad spectrums of polymers; natural polymers, synthetic polymers, organic polymers as well as silicones are used in a wide range of cosmetic and personal care products as film-formers, emulsifiers, thickeners, modifiers, protective barriers, and as aesthetic enhancers.

A further embodiment features a method of making liposomes comprising forming a mixture of multilamellar vesicles and a CF. The mixture is decompressed to remove the CF to form one or more liposomes or niosomes.

Preferably, multilamellar vesicles are made by hydrating phospholipids in an aqueous phase. Preferably, the aqueous phase or the phospholipids contain a cosmeceutical therapeutic agent.

EXAMPLE 1

Phase Behavior Studies for the Low Pressure Low Temperature Alternative Construction of a Liposome and Niosome Vesicles (LPLTVs)—CO2-Solvent System Prior to liposome or niosome formation, the phase behavior and solubility of the chosen lipid in dense $CO_2$ were investigated to verify the suitability of the lipid for dense gas processing and, in particular LPLTVs processing.

Knowledge of the threshold pressure for precipitation of lipid from solution is also a key factor for design of the LPLTVs process in order to determine the maximum pressure for the technique so that yield is enhanced and loss of lipid in the expansion chamber minimized. The solid state of 1,2 distearoyl-sn-glycero-3-phosphocholine (DSPC) was maintained when the lipid was exposed to CO2 below 350 bar at 50° C. and 150 bar at 70° C. The solubility of DSPC in pure CO2 at 50° C. and pressures up to 280 bar was considered negligible. The addition of 5 mol % ethanol co-solvent did not significantly improve the solubility of DSPC in CO2 at 50° C. and 250 bar. Use of higher pressures or larger amounts of organic solvent are undesirable, thus the results of the solubility study are in agreement with the literature in concluding that effects arising from poor solubility of lipids in dense CO2 are not easily overcome.

In prior art, at 50° C. and 250 bar, DSPC required the addition of 4.8% v/v ethanol as well as the use of a recycling system for homogeneous dissolution of the lipid in CO2. In the current embodiment, the use of the LPLTVs process eliminates the current limitations of dense gas techniques associated with solubilizing lipids using a supercritical fluid and simply utilizes a dense gas as an aerosolization aid. The threshold pressure for the precipitation of DSPC from a 10 mg/mL ethanol solution at 22° C. was 55 bar.

Precipitation was first observed at 58, 55, and 56 bar for the 5, 10, and 20 mg/mL solutions of DSPC and cholesterol (70:30 lipid to cholesterol weight ratio) in ethanol at 22° C., respectively. Therefore it can be seen that cholesterol had negligible effect on the threshold pressure. When the pressurization rate for the 5 mg/mL lipid/cholesterol solution was dramatically increased, precipitation was not observed until 60 bar was reached. A faster pressurization rate is preferable for the embodiments LPLTVs process in order to minimize the time requirement for each experiment. During this experiment, noticeable expansion only started to occur after 50 bar was reached. Solution expansion is desired to maximize the effect of utilizing CO2 as an aerosolization aid to disperse the lipid solutions throughout the aqueous phase. Therefore, the expansion pressure used in the LPLTVs experiments to avoid solute precipitation and enhance the yield for or niosome formation from ethanol solutions was between 50 and 55 bar at 22° C.

The threshold pressure for the precipitation of a 20 mg/mL DSPC/cholesterol chloroform solution (90:10 lipid/cholesterol weight ratio) at 22° C. was 41 bar. The solvent volume had significantly expanded (doubled) by the time 40 bar was reached in the chloroform experiments. Therefore, expansion pressures between 38 and 40 bar were used for the LPLTVs chloroform experiments to achieve maximum expansion without lipid precipitation.

EXAMPLE 2

Effects of Process Variables on LPLTVs Operation

The effects of solute composition, solute concentration, type of solvent, nozzle diameter, type of aqueous media, temperature of vesicle formation chamber, and volume of dense gas used for spraying on both the ease of operation of the embodiments LPLTVs process and the product were investigated. The results obtained for liposome formation are summarized in Table 1. Preliminary trials were conducted to establish viable nozzle options for the LPLTVs system. A variety of nozzles were tested including 102, 178, 254, 508, and 1016 μm i.d. stainless steel tubing and 100 μm i.d. Peeksil tubing (polymer tubing with fused silica lining). The most suitable nozzle for the LPLTVs apparatus, to control the flow rate and prevent blockages, was the 178 μm i.d. stainless steel tubing. The 254 μm nozzle was used in Set 1 (Table 1); however, there were difficulties in controlling the flow rate and maintaining constant pressure in the expansion chamber. Other nozzle dimensions may be selected depending on the pump capacity and vessel dimensions.

The LPLTVs process of the present example embodiment is robust and, within the range examined, variation of solute concentration and composition, type of solvent, type of aqueous media, and volume of CO2 used for spraying had minimal effect on the operation of the LPLTVs process. The temperature of the vesicle formation chamber did, however, significantly affect the process since a smaller amount of liposomal product was obtained at 90° C. (Set 5) compared with 75° C. The smaller volume can be attributed to the aqueous medium being closer to its boiling point at 90° C., and thus some of the water was lost to the solvent trap via evaporation.

EXAMPLE 3

Characterization of Liposomes Produced by the LPLTVs Process

The Liposome Morphology.

TEM (Transmission electron microscopy) was used to investigate the morphology of the particles produced in the embodiments LPLTVs process. At all conditions studied, submicron spheres were observed that possessed a similar structure to liposomes previously reported in the literature. The image shown in FIG. 5.0 indicates that spherical particles, generally ranging in size from 35 to 200 nm and more commonly 35-100 nm, were formed using the LPLTVs process. Images collected suggest that the liposomes were unilamellar. Not only were the spheres of a size range common to unilamellar liposomes, but in many images a single, thin wall can be seen at the edge of each particle. However, the arguments against positive identification of lamellarity using negative staining and TEM have been well documented in the literature.18 Staining artifacts are difficult to identify and are often interpreted as unexpected morphologies. Confirmation that the particles formed were in fact liposomes was found by utilizing SANS (Small-Angle Neutron Scattering) to identify an aqueous core, as discussed below. The spherical particles shown in FIG. 5.0 are a general indication of the liposomes formed; however, some other features have also been observed. In several samples, a large quantity of smaller spherical particles (10-20 nm) was observed, which are at or below the lower size limit at which liposomes can be formed and may be considered as micelles. In some samples, small vesicles appear to be aggregated into or contained within a larger liposome vesicle, as shown in FIG. 6.0.

A vesicle-in-vesicle structure may be formed in the last stage of the LPLTVs process due to liposomes forming in the presence of existing vesicles. However, the lipid vesicles are more likely to have formed into aggregate structures during the negative staining process in order to minimize any deleterious effects when the aqueous phase was removed or to minimize the interactions of the lipid with the stain. The artifact of these aggregated systems could also result from a larger vesicle superimposed upon smaller vesicles, which is a common feature in TEM analysis. The particle size and morphology of the LPLTVs liposomes was not significantly changed within the range of process parameters varied. However, rods or coffee bean morphology (liposomes exhibiting a characteristic 'coffee-bean' appearance due to the presence of an inner structure apparently separating the LUV into two sections) appeared in a few samples in addition to spherical particles, as shown in FIG. 7.0. It is suggested that the coffee bean morphology was formed due to the collapse of vesicles, predominantly for the smaller particles. This effect can be attributed to the lower stability of small vesicles due to the high curvature of the membrane.

The unilamellar liposomes produced using a conventional technique were stained with ammonium molybdate with and without the presence of protein. The images of the liposomes stained without protein showed "cup-like structures" and vesicles consisting of two lipid membranes. When protein was included in the staining process, the images showed vesicles consisting of a single lipid bilayer.

In the present embodiment, it is concluded that the liposomes in both images were unilamellar and that the vesicles had collapsed in the absence of protein. The double membrane feature can therefore be explained by the thick edge of the collapsed sphere, and the "cup-like structures" can be observed if the collapsed spheres are rotated.

The correct choice of vesicle or niosome preparation method in the current embodiment depends on the following parameters: the physicochemical characteristics of the material to be entrapped and those of the liposomal or niosomal ingredients; the nature of the medium in which the vesicles are dispersed; the effective concentration of the entrapped substance and its potential toxicity; additional processes involved during application/delivery of the vesicles; optimum size, polydispersity and shelf-life of the vesicles for the intended application; and, batch-to-batch reproducibility and possibility of large-scale production of safe and efficient liposomal products.

TABLE 1

Summary of the Conditions Investigated and the Results Obtained for Producing Liposomes via the embodiments of the LPLTVs Process.

| set | 1 | 2 | 3 | 4 | 5 | 6 | 7 | 8 | 9 |
|---|---|---|---|---|---|---|---|---|---|
| nozzle diameter (µm) | 254 | 178 | 178 | 178 | 178 | 178 | 178 | 178 | 178 |
| solute lipid content (% w/w) | 70 | 70 | 90 | 90 | 90 | 90 | 90 | 90 | 90 |
| solute conc. (mg/mL) | 20 | 20 | 20 | 5 | 20 | 20 | 20 | 20 | 20 |
| VFC temp. (° C. ± 2.5) | 75 | 75 | 75 | 75 | 90 | 75 | 75 | 75 | 75 |
| $CO_2$ spraying vol. (mL) | 200 | 200 | 200 | 200 | 200 | 50 | 200 | 200 | 200 |
| aqueous media | RO $H_2O$ | RO $H_2O$ | RO $H_2O$ | RO $H_2O$ | RO $H_2O$ | RO $H_2O$ | DI $H_2O$ | TBS | RO $H_2O$ |
| organic solvent | EtOH | EtOH | EtOH | EtOH | EtOH | EtOH | EtOH | EtOH | Chlfm |
| effective diameter (nm) | 156 ± 2 | 166 ± 5 | 121 ± 1 | 162 ± 23 | 207 ± 75 | 122 ± 2 | 119 ± 3 | 143 ± 5 | 387 ± 64 |
| polydisperity | 0.27 ± 0.01 | 0.27 ± 0.01 | 0.15 ± 0.01 | 0.19 ± 0.01 | 0.18 ± 0.01 | 0.15 ± 0.01 | 0.17 ± 0.02 | 0.18 ± 0.02 | 0.29 ± 0.03 |
| product lipid content (% w/w) | 75.2 ± 1.9 | 77.3 ± 1.8 | 82.4 ± 0.4 | 76.1 ± 0.1 | 81.8 ± 0.5 | 80.5 ± 0.2 | 80.9 ± 0.3 | 80.1 ± 0.6 | 81.8 ± 1.3 |
| residual solvent (% v/v) | 3.1 ± 0.4 | 1.6 ± 0.8 | 1.4 ± 0.4 | 2.2 ± 0.3 | 1.9 ± 0.7 | 3.9 ± 0.2 | 1.8 ± 0.4 | 2.0 ± 0.8 | 0.4 ± 0.3 |

*VFC: vesicle formation chamber,
RO $H_2O$: water purified via reverse osmosis;
DI $H_2O$: deionized water;
TBS: TRIS buffered saline;
EtOH: ethanol;
Chlfm: chloroform Collapsed spheres were present in all LPLTVs samples; however, rods or "coffee bean" particles were rare except in those samples from Sets 1 and 2, where a higher proportion of cholesterol was used compared with other samples.

TABLE 2

The calculated SLD for the components LPLT Vs of the LPLT Vs liposome samples

| material | SLD (× $10^{-6}$ Å$^{-2}$) |
|---|---|
| $H_2O$ | −0.56 |
| $D_2O$ | 0.33 |
| hydrocarbon Chain $(CH_2)_n$ | −0.44 |
| cholesterol $(C_{27}H_{45}OH)$ | 0.21 |
| lipid headgroup $(C_{10}H_{13}O_8NP)$ | 1.12 |

TABLE 3

SANS Fitted parameters for the LPLT liposome sample

| fitted parameter (Å$^{-2}$) | value |
|---|---|
| Core SLD | 6.30 × $10^{-6}$ |
| Shell SLD | 3.85 × $10^{-6}$ |
| Solvent SLD | 6.82 × $10^{-6}$ |

Cholesterol was incorporated in order to improve stability, and it has been reported in the literature that the incorporation of cholesterol causes larger liposomes or niosomes to form.

However, the rod-shaped particles were at the smaller end of the size range for the LPLTVs. Comparison of images from a number of samples indicated that the presence of rods may be promoted by the level of stain as well as the size of the vesicles. It is therefore also possible that the relative proportion of rods found in Sets 1 and 2 was amplified by the staining process. Because of the improved spherical morphology observed in Set 3, the experiments were carried out using a preferred lipid/cholesterol ratio of 90:10.

Advantages of the Current Embodiments LPLTVs Process for Bulk Liposome or Niosome Vesicle Formation.

The LPLTVs process has many advantages over conventional liposome or niosome formation techniques. These advantages include the fact that it is a simple and rapid process for bulk production of unilamellar liposomes or niosomes. A conventional liposome standard was produced, and the formation process took almost 24 h and multiple stages to complete. The embodiments LPLTVs process produced a greater volume of the same formulation in less than half an hour, clearly demonstrating the dramatic reduction in processing time.

The conventional ethanol and ether injection methods exhibit some similarities to the embodiments LPLTVs process since they involve the dissolution of a lipid into an organic phase, followed by the injection of the lipid solution into aqueous media forming liposomes. The drawbacks of the ethanol injection method as opposed to the examples of the present embodiment, are the poor homogeneity of the vesicles if there is not adequate mixing and the residual solvent levels in the product.

Either injection method eliminates the residual solvent issue by having a heated aqueous phase, but is a time-consuming technique. It has been suggested that injecting the ether solution at a rate faster than 0.2 mL/min can cause cooling of the aqueous phase due to evaporation, and that pre-evaporation of ether can cause nozzle blockages and the formation of multilamellar vesicles. The LPLTVs process of the present embodiment for the formation of liposomes or niosomes formed around cosmeceutically benevolent ingredients has significant advantages over both the ethanol and ether injection methods since the depressurization from a high pressure environment creates outstanding dispersion of the lipid solution and mixing with the aqueous environment. The incorporation of both heating and dense gas washing enables the solvent to be efficiently removed. The LPLTVs process can also produce an equivalent volume of product in a significantly reduced time span. Compared with other dense gas processes developed for liposome formation, the LPLTVs process is beneficial due to its simplicity and the incorporation of residual solvent removal measures into the method. The LPLTVs process also operates at pressures generally less than 60 bar and moderate temperatures, therefore making the process more cost-effective and avoiding the concerns of uncontrollable foam formation present in the low pressure liposome method. A significant advantage of the LPLTVs process is that it can be used to process a broad range of materials since there is no requirement for the compound to be solubilized in the dense gas and there are no high shear forces. Furthermore, time-consuming solubility studies and recycling loops for lipid solubilization are not needed. The only preliminary investigation required is the determination of the threshold pressure for precipitation of the solutes from expanded solution, such that the solution expansion can be carried out without precipitation.

In the LPLTVs process of the current embodiment, the entrapment of hydrophilic compounds may be achieved through the dissolution of the target compound into the aqueous media prior to release of the lipid solution. The liposomes or niosomes would then form, entrapping the hydrophilic or hydrophobic compound within the aqueous interior of the vesicle.

To entrap a hydrophobic, hydrophilic, lipophilic, or amphipathic compound into liposomes or niosomes using the LPLTVs process, the compound is dissolved along with the phospholipid and other solutes in the liquid solvent.

The compound then becomes entrapped within the phospholipid membrane as a result of the affinity of the compound for the membrane rather than the aqueous phase.

The suitability of the LPLTVs process for entrapping hydrophobic compounds has already been demonstrated through incorporating up to 25% w/w cholesterol into the liposome formulation. The LPLTVs technique can also be applied to the formation of structures other than liposomes. Micro particles of hydrophobic compounds could be produced through precipitation into aqueous media in the LPLTVs process.

Liposomal Particle Size Distribution and Stability. Photon correlation spectroscopy (PCS) was used to assess the particle size distribution of the liposomal population using the Brookhaven ZetaPlus. Each liposomal sample was diluted in RO or DI water and placed in a disposable polypropylene cuvette. Ten runs, each of 1 min duration, were conducted at 23-25° C. for each sample. A laser wavelength of 678 nm was used with a destination angle of 90°. The dust cutoff was set between 20 and 50 μm. The instrument calculates an effective diameter for each run and an overall effective diameter for the 10 runs combined. The effective diameter is the mean diameter that is calculated by the following equation:

$$\text{Effective diameter} = \left(\frac{1}{d_k}\right)^{-1} = \frac{\sum_i N_i d_i^6 P_i}{\sum_i N_i d_i^5 P_i}$$

Where $N_i$ refers to the number per scattering volume of the ith particle, and $P_i$ accounts for angular scattering effect for particles larger than $\lambda/20$. $P_i$ is calculated using Mie theory and requires the particle refractive index; however, for Rayleigh scatters and at sufficiently low angles, $P_i=1$ is used in the program.

EXAMPLE 4

A Formulation for the Treatment of Acne Made Using the Current LPLTVs Embodiment A solution for treating Acne vulgaris or Propionibacterium acnes containing lipids formed of the following ingredients utilizing the science of the present embodiment may be formulated using the constructed phospholipids of the following volumes;

D.I. water 50% to 95% (preferably 60 to 90%, ethanol 15 to 40% (preferably 25 to 30%), hyaluronic acid 5 to 50% (preferably 12 to 18%) propanediol 10 to 80% (preferably 20 to 25%), aloe vera 0.2 to 20% (preferably 0.5 to 5%), azelaic acid 2 to 50% (preferably 4 to 8%), salicylic acid 0.2 to 20% (preferably 0.5 to 5.0%), lauric acid 0.2 to 20%

(preferably 0.5 to 5.0%), asorbyl palmitate 0.1 to 20% (preferably 0.2 to 8%) niacinimide 0.2 to 20.0% (preferably 0.5 to 5%), lecithin 0.2 to 10% (preferably 0.5 to 5.0%), glycerin 0.5 to 25% (preferably 2 to 10%), caffeine 0.2 to 20% (preferably 0.5 to 10%)

EXAMPLE 5

A Formulation for the Enhanced Hydration and the Reduction of Fine Lines and Wrinkles Made Using the Current Embodiment A solution for treatment of lack of skin hydration and the reduction of fine lines and wrinkles containing lipids formed of the following ingredients utilizing the science of the present embodiment may be formulated using the constructed phospholipids of the following volumes; D.I. water 50% to 95% (preferably 60 to 90% ethanol 15 to 40% (preferably 25 to 30%), hyaluronic acid 5 to 50% (preferably 12 to 18%) propanediol 10 to 80% (preferably 20 to 25%), aloe vera 0.2 to 20% (preferably 0.5 to 5%), hexa-peptide 8 2% to 50% (preferably 5% to 20%), caffeine 0.2 to 20% (preferably 0.5 to 10%), glycerin 0.5 to 25% (preferably 2 to 10%), tocopheryl acetate 0.1 to 10% (preferably 0.5 to 8%), retinyl palmitate 0.1 to 10% (preferably 0.5 to 8%), asorbyl palmitate 0.1 to 20% (preferably 0.2 to 8%), Copper tripeptide GHK-Cu 0.1 to 20% (preferably 0.2 to 8%), hesperidin 0.1 to 20% (preferably 0.2 to 8%), dimethylethanolamine (DMAE) 0.05 to 20% (preferably 0.08 to 8%), sesame oil 2 to 50% (preferably 3 to 20%) beta glucan 0.1 to 20% (preferably 0.2 to 8%)

TEST 1

LPLTVs Method for the Preparation of Hyaluronic Acid-rich Vesicles

The present embodiment is based on the use of compressed $CO_2$ in a process called LPLTVs for the production of micron-sized and submicron-sized crystalline particles from an organic solution. As novelty the process used the $CO_2$ as co-solvent being completely miscible at a given pressure and temperature with a specific solution of an organic solvent containing the solute to be crystallized. In order to take full advantage of compressed fluid processing without using severe working conditions a novel and improved procedure based on the LPLTVs process was developed. This method, named as LPLTVs (Low Pressure Low Temperature alternative construction of Liposome Vesicles), enabled the preparation of cholesterol rich-hyaluronic acid vesicles. The process uses milder conditions of pressure (<10 MPa) and temperature (<308 K) than the previously described methodologies based on CFs, allowing the processing of heat labile compounds and reducing the investment cost of a high pressure plant when the process is scale-up. Using this procedure, homogeneous nanovesicles composed of hyaluronic acid, cholesterol and the cationic surfactant CTAB (cetyltrimethylammonium bromide, in a molar ratio 1:1, were prepared by depressurizing a volumetric expanded organic solution containing the cholesterol and hyaluronic acid over a flow of an aqueous solution containing the CTAB surfactant (FIG. 5.0). An alternate non-ionically formed elastic noisome can be constructed using the same apparatus.

During the depressurization step, the expanded organic solution experiences a large, abrupt and extremely homogenous temperature decrease produced by the $CO_2$ evaporation from the expanded solution. This explains the obtaining of homogenous vesicles regarding size, lamellarity and morphology.

In order to prepare any vesicular system using LPLTVs is necessary that the lipids forming the membrane are completely soluble in the CO2-expanded organic solvent, presenting one phase at the working conditions of pressure, P w, temperature, T w and CO2 molar fraction, X2. Therefore for the preparation of cholesterol rich-hyaluronic acid vesicles by LPLTVs method is always necessary to analyze the solubility behavior of the used sterol in CO2-expanded solvents, by means of a detailed phase diagram study, like the one showed in FIG. 6.0.

An important prerequisite for the effective use of vesicles as a cosmeceutical ingredient carrier as described above is to control their stability, which can be defined as the extent to which the carrier retains its ingredient contents either in vitro or in vivo studies. One of the major disadvantages when using classical vesicles based on phospholipids, is the leakage of the encapsulated ingredient during their storage. One variant that can enhance the retention of drugs and promote the stability of liposomes or niosomes is the presence of hyaluronic acid in the formulation. Another variant is the preparation of liposomes from non-phospholipid amphiphiles, such as surfactants or polymers.

This kind of vesicular formulations show low passive leakage in comparison to liposomal systems based only on phospholipids and therefore a higher retention of the encapsulated materials, as for example epi-dermal therapeutically active molecules.

In the present example embodiment for the preparation of positively charged vesicles composed by cholesterol, hyaluronic acid and the cationic surfactant hexadecyltrimethylammonium bromide (CTAB). More recently nanoscopic vesicles, composed by different sterols and other quaternary ammonium surfactants have been also successfully prepared. This is why it was decided to name this kind of formulations as LPLTV (low pressure low temperature vesicles) that are stable for periods as long as several years, their morphology do not change upon rising the temperature or by dilution and they show a great homogeneity regarding size and morphology.

Studies at molecular level of the self-assembling of cholesterol hyaluronic acid and CTAB molecule in aqueous medium showed that a pure vesicular phase is only formed at equimolar ratios of both components. Moreover molecular dynamic (MD) simulations revealed that the cholesterol, hyaluronic acid and the CTAB self-assemble in a unique bimolecular synthon that can be considered as a single entity which further self-assembles in particularly stable vesicles (FIG. 7.0) (FIG. 10). Moreover, MD simulations have provided a theoretical support to justify the experimental high thermal stability and the exceptional morphological properties attributed to cholesterol, hyaluronic acid/CTAB vesicles at 1:1 molar ratio.

TEST 2

Analysis of Active and Placebo Tape Strips from an In-Vivo Study of Skin Permeation of 800 KDa Hyaluronic Acid Using the Embodiments LPLTVs Formation Process Introduction The test was to extract and analyze tape strips and blanks from an in vivo tape stripping study of 800 KDa Hyaluronic Acid skin penetration transport.

HA distribution in stratum corneum (SC) layer was investigated. Distribution in SC was studied using a tape-stripping method.

Methods:

Each tape sample will be extracted individually by extraction solvent: 1×PBS with 0.2% NaN3/acetonitrile (50/50 v). Samples with extraction solvent were vortexed at high speed for 1 minute followed with centrifugation at 12,000 rpm for 10 minutes (chill the samples on ice at 4° C. and then centrifuge). The supernatant solution was then collected from each tube/container and stored at 4° C. and ready for analysis.

Outcome:

See the chart in FIG. 11.0 showing Hyaluronic Acid levels in active and control samples.

Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method for the construction of cosmeceutically bioactive compositions including elastic niosome vesicle epi-dermal delivery vehicles without use of supercritical $CO_2$ and in a continuously operating process, the method comprising:
    forming a liposome solution or mixture of cosmeceutically benevolent phospholipids, the solution being hydrophobic or hydrophilic, the solution including an ingredient from the group consisting of a natural ingredient and a synthetic ingredient, the solution having an aqueous phase;
    removing any constituent attributes of water-insolubility from the solution, while operating under conditions to preserve activity of labile biomolecules;
    loading the liposome solution and desired hydrophobic bio-actives into an organic solvent residing in a pressure reactor, the pressure reactor having been previously driven to a working temperature less than 31.1° C.;
    pressurizing the reactor with compressed $CO_2$ until reaching a working pressure less than 73.8 bar to produce a resulting $CO_2$-expanded solution, the reactor maintaining a pressure and temperature to prevent the $CO_2$ from going supercritical; and
    depressurizing the resulting $CO_2$-expanded solution over an aqueous phase to form vesicular conjugates, the resulting solution containing water soluble cationic or non-ionic surfactants and hydrophilic or hydrophobic bio-actives, wherein an emulsion further comprises a water-soluble or fat-soluble cosmetic or cosmeceutical active ingredient.

2. The method of claim 1 wherein the phospholipids are selected from the group consisting of: a nonionic amphiphilic lipid, an ionic amphiphilic lipid, a mixture of nonionic lipids, and an ionic lipid.

3. The method of claim 1 wherein the phospholipids are of the phosphate group of phosphatidylcholine (PC) amphiphilic molecules, having a polar head group and a lipophilic tail, and are esterified with an additional alcohol of choline possessing a zwitterionic isoelectric point and are negatively charged at higher pH values and positively charged at lower pH values.

4. The method of claim 1 wherein the phospholipids are of the phosphate group phosphatidylethanolarnine (PE), and are esterified with an additional alcohol of ethanolarnine and are a neutral charged zwitterionic.

5. The method of claim 1 wherein the phospholipids are of the phosphate group phosphatidylglycerol (PG) with glycerol being anionic in charge.

6. The method of claim 1 wherein the phospholipids are of the phosphate group consisting of a ceramide unit with a phosphorylcholine moiety attached, and a sphingolipid analogue of phosphatidylchol, or sphingomyelin, or ceramide phosphorylcholine.

7. The method of claim 1 wherein the phospholipids are amphiphilic liposomes wherein the molar ratio of the mixture of cholesterol and at least one neutral or zwitterionic lipid is between 8 and 0.15.

8. The method of claim 1 wherein the phospholipids include at least one non-ionic amphiphilic lipid being an ester of at least one polyol, said ester being a polyethylene glycol containing from 0.5 to 70 ethylene oxide units, sorbitan, glycerol containing from 1 to 35 ethylene oxide units, polyglycerol containing from 1 to 18 glycerol units, or a fatty acid containing at least one saturated or unsaturated, linear or branched, C8-C22 alkyl chain.

9. The method of claim 1 wherein at least one cationic amphiphilic lipid is present in the liposome solution or mixture in a concentration ranging from 0.5 to 65% by weight with respect to the total weight of the amphiphilic lipid phase.

10. The method of claim 1 including using a formation of unilamellar vesicles having one lipid bilayer between 50-250 nm enclosing a large aqueous core, and multilamellar vesicles having two or more concentric lipid bilayers between 1-5 μm.

11. The method of claim 1 including using cholesterol to anchor phosphate group phosphatidylcholine (PC) amphiphilic molecules, the phosphate group phosphatidylethanolarnine (PE) molecules, and the phosphate group phosphatidylglycerol (PG) molecules.

12. The method of claim 1 including using an amphiphilic liposome having neutral lipids wherein said neutral lipids are selected from the group consisting of cholesterol or mixtures of cholesterol and at least one neutral or zwitterionic lipid.

13. The method of claim 1 including using an amphiphilic liposome having phosphatidylcholine selected from DMPC, DPPC, DSPC, POPC, DOPC, soy bean PC or egg PC.

14. The method of claim 1 including using an amphiphilic liposome having K neutral of a mixture of cholesterol and at least one neutral or zwitterionic lipids.

15. The method of claim 1 including using an amphiphilic liposome having a mixture of cholesterol and at least one neutral or zwitterionic lipid selected from the group consisting of: cholesterol/phosphatidylcholine, cholesterol/phosphatidylethanolamine, and cholesterol/phosphatidylethanolamine/ phosphatidylcholine.

16. The method of claim 1 including using an amphiphilic liposome having a mixture of lipid components with amphiphilic properties and wherein said mixture of lipid components comprises at least one pH responsive component.

17. The method of claim 1 including using an amphiphilic liposome that encapsulates at least one active agent.

18. The method of claim 1 including using an amphiphilic liposome wherein at least 80 wt. percentage of an active agent is disposed inside said liposomes.

19. The method of claim 1 including liposomes being non-encapsulated active agents.

20. The method of claim 1 including forming a cosmeceutical composition comprising active agent-loaded amphiphilic liposomes and a cosmeceutically acceptable vehicle therefor.

21. The method of claim 1 including using amphiphilic liposomes in vitro, in vivo or ex-vivo transfection of cells.

* * * * *